United States Patent [19]
Schmitt et al.

[11] Patent Number: 5,865,853
[45] Date of Patent: Feb. 2, 1999

[54] COMPOSITION FOR DYEING KERATIN FIBERS CONTAINING VEGETABLE DYES, A DIRECT DYE COMPOUND AND OIL AND METHOD OF DYEING HAIR USING SAME

[75] Inventors: Manfred Schmitt, Heppenheim; Uwe Lenz, Zwingenberg; Wolfgang Balzer, Alsbach; Henk Niessink, Darmstadt, all of Germany

[73] Assignee: Wella Aktiengesellschaft, Darmstadt, Germany

[21] Appl. No.: 846,663

[22] Filed: May 1, 1997

[30] Foreign Application Priority Data

May 9, 1996 [DE] Germany .................. 196 18 653.6

[51] Int. Cl.⁶ ..................................... A61K 7/13
[52] U.S. Cl. .................. 8/405; 8/435; 8/527; 8/528; 8/580; 132/208
[58] Field of Search ................. 8/404, 405, 414, 8/415, 424, 425, 426, 428, 435, 524, 526, 527, 528, 580, 581, 638, 639, 643, 644, 646, 657, 662, 617, DIG. 1; 132/208; 424/70.6, 70.7, 74

[56] References Cited

U.S. PATENT DOCUMENTS

| | | | |
|---|---|---|---|
| 406,071 | 7/1889 | Vogt | 8/405 |
| 1,341,637 | 6/1920 | Fries | 8/524 |
| 1,636,341 | 7/1927 | Wheeler | 8/524 |
| 3,369,970 | 2/1968 | McLaughlin et al. | 8/528 |
| 3,811,830 | 5/1974 | DeMarco | 8/405 |
| 4,069,013 | 1/1978 | Hett et al. | 8/524 |
| 4,184,843 | 1/1980 | Baumann | 8/405 |
| 4,358,286 | 11/1982 | Grollier et al. | 8/405 |
| 4,402,702 | 9/1983 | Kaspar et al. | 8/524 |
| 4,602,913 | 7/1986 | Grollier et al. | 8/405 |
| 4,888,026 | 12/1989 | Lang et al. | 8/405 |
| 4,895,575 | 1/1990 | Hocquaux et al. | 8/405 |
| 4,933,177 | 6/1990 | Grollier et al. | 8/405 |
| 4,938,954 | 7/1990 | Gross et al. | 8/405 |
| 5,110,318 | 5/1992 | Altobelli et al. | 8/405 |
| 5,259,849 | 11/1993 | Grollier et al. | 8/405 |
| 5,447,538 | 9/1995 | Rosenbaum et al. | 8/405 |
| 5,601,620 | 2/1997 | Ishikawa | 8/405 |

FOREIGN PATENT DOCUMENTS

0630643A1  8/1994  European Pat. Off. .
2030581   11/1970  France .

OTHER PUBLICATIONS

Waters; Color Your Hair; Holt, Rinehart and Winston; pp. 94–99, 1984 No Month Available.

Spencer, Hair Coloring A Hands–On Approach, Milady Publishing Company, pp. 59–68, 1990 No Month Available.

Redgrove et al., Hair–Dyes and Hair–Dyeing Chemistry and Technique, Chemical Publishing Co., Inc., pp. 59–87, 122–126 and 103, 1939 No Month Available.

*Primary Examiner*—Paul Lieberman
*Assistant Examiner*—Caroline D. Liott
*Attorney, Agent, or Firm*—Michael J. Striker

[57] ABSTRACT

The composition for dyeing keratin fibers is mixed with water prior to use and contains from 35 to 75 percent by weight of at least one powdery vegetable dye material; from 25 to 65 percent by weight of at least one oil; and from 0.001 to 15 percent by weight of a physiologically unobjectionable nitro dye compound, azo dye compound, quinone dye compound and/or a triphenylmethane dye compound. A method of dyeing hair using this composition is also described.

11 Claims, No Drawings

COMPOSITION FOR DYEING KERATIN FIBERS CONTAINING VEGETABLE DYES, A DIRECT DYE COMPOUND AND OIL AND METHOD OF DYEING HAIR USING SAME

The present invention is related to the invention disclosed in copending U.S. patent application Ser. No. 08/848,308 filed Apr. 30, 1997.

BACKGROUND OF THE INVENTION

The present invention relates to a composition for dyeing keratin fibers based on vegetable dyes and direct-dyeing dye compounds and to a method of dyeing hair using this composition.

Vegetable dyes are used to an increasing extent for dyeing of keratin fibers, especially human hair, since these dyes permit a safe dyeing of keratin fibers.

The vegetable dyes are used in the form of a powder or granulate, which is mixed prior to use with water.

However several disadvantages are associated with the use of this type of vegetable dye powder and/or vegetable dye granulate, which can contain many ingredients.

Separation of component ingredients frequently occurs in vegetable dye powders or vegetable dye granulate mixtures of several granulates containing raw materials of different densities during transport or storage. The heavier ingredients sink into the lower portion while the lighter ingredients collect in the upper portion. This separation has the consequence that equal amounts of granulate or powder taken from different locations have different compositions and thus can have different dyeing properties.

In order to avoid this separation it is necessary to shake the powder or granulate prior to taking a portion of it to avoid this separation problem. However often the user does not do that.

A separation can be prevented also by use of powder mixtures with very fine grain size. This however has the disadvantage that this type of powder mixture—especially during opening of the container, removal of a portion of the powder or during mixing with water—is inclined to generate a large amount of dust.

Furthermore should, for example, vegetable granulates be used comprising granulates which are indeed dust-free and more or less compact in accordance with the method used to produce them, fine dust may still form by friction of the granulates with each other, especially during transportation.

The prepared vegetable dye slurries or pastes obtained with the above-named powders and granulates also have application-specific disadvantages. They are difficult to apply and have poor adherence to the hair. During the acting time the dye mass dries and crumbles away. The vegetable dye paste or slurry formed also has poor rinsibility.

Numerous attempts have already been made to solve this problem.

Published European Patent Application 0 630 643 (EP-OS 0 630 643) discloses producing a pourable powder by using a special granulation process with addition of waxes having a flow point of 40° C. to 130° C. and thus to reduce the dusting. Dusting cannot be totally avoided using this powder however, especially during transfer of the vegetable dye powder into a stirring vessel and during mixing of the vegetable dye powder with water. Furthermore depending on the employed wax the miscibility of this dye powder with water is very variable and often unsatisfactory.

An additional problem with vegetable hair dye compounds is the poor color coverage of the hair dye compositions based on them.

Although numerous attempts have been made to find hair dye compositions based on vegetable dye ingredients which overcome these problems, a satisfactory composition of this type has not been found until now.

SUMMARY OF THE INVENTION

It is an object of the present invention to provide a vegetable dye which does not have the above-described disadvantages, especially which is dust-free and, at the same time, has good miscibility and good properties for the application for which it is used, especially in regard to its dyeing properties, especially in regard to color coverage and intensity of the color of the fibers dyed with the composition.

Surprisingly it has been found that the above-described objects can be attained by a suspension-, emulsion- or dispersion-like vegetable dye composition according to the invention, which also contains direct-dyeing dye compounds.

The composition according to the invention for dyeing keratin fibers, especially hair, based on vegetable dye materials, comprises a dye-containing suspension (which is designated as a dye-containing dispersion or a dye-containing emulsion) containing at least one powdery vegetable dye ingredient, at least one oil and at least one direct-dyeing dye compound.

Ground and/or pulverized vegetable dye ingredients such as Henna leaves, indigo leaves, camomile, curcuma roots, rhubarb, black alder tree bark(*Rhamanus frangula L.*), olive leaves, Canadian bloodroot, curcuma(*Curcuma Longa L.*), fustic, redwood, red sandalwood, haematoxylon wood (*Haematoxylon campechianum L.*), madder root (*Rubia tinctorum L.*), black elder or black apple berries, can be used. The vegetable dye ingredients in the dye-containing suspension according to the invention can be contained there in a total amount of 35 to 75 percent by weight, especially 40 to 60 percent by weight.

As oils, especially liquid silicones or paraffins, vegetable or animal oils, liquid fatty acids, liquid fatty acid esters, liquid alkoxylated fatty acid esters, liquid glycerides, liquid alkoxylated glycerides, liquid fatty alcohols, liquid alkoxylated fatty alcohols, especially liquid ethoxylated fatty alcohols ethoxylated with 2 to 5 Mol ethylene oxide units, liquid polyhedric alcohols, liquid nonylphenol ethers, liquid polyethylene glycols or liquid polypropylene glycols.

Examples of suitable oils, fluid at room temperature (25° C.), include the following oils: Paraffinum perliquidum, Paraffinum subliquidum, dimethicone, cyclomethicone, isopropyl palmitate, hexyllaurate, dibutyl adipate, octyl palmitate, polyethylene glycol(7) glyceryl cocoate, isopropyl myristate, isopropyl stearate, trioxyethylene lauryl ether, dioxyethylene lauryl ether, oleic acid, trilaurin, oleyl alcohol, sunflower oil, spermaceti oil, olive oil and castor oil. The use of isopropyl palmitate, sunflower oil, olive oil and castor oil is particularly preferred. Preferably the dye is free of waxes; however small amounts, a maximum or up to 5 percent by weight, of waxes may be added, if the cream-like consistency of the dye-containing suspension is not impaired.

The dye-containing composition according to the invention contains from 25 to 65 percent by weight, advantageously 35 to 60 percent by weight, of the oil or wax, based on the total amount of the dye-containing suspension.

The direct-dyeing dye compound can be a naturally-occurring dye compound, e.g. lawsone (2-hydroxy-1,4-naphthoquinone) or juglone (5-hydroxy-1,4-naphthoquinone). It can also be a conventional, physiologically unobjectionable, dye compound selected from the group consisting of nitro dye compounds, azo dye compounds, quinone dye compounds and triphenyl-methane dye compounds. In particular the direct-dyeing dye compound can be, for example, 3-[(4'-amino-2-chloro-5'-nitrophenyl)amino]-1,2-propandiol, 3,3'-[(2"-chloro-5"-nitro-1",4"-phenylene)-diamino-bis-1,2-propandiol, 2-(4'-amino-3'-nitroanilino)-ethanol, 4,N-Ethyl,N-(2'-hydroxyethyl)amino-1-(2"-hydroxyethyl)amino-2-nitrobenzene, 1-amino-3-methyl-4-(2'-hydroxyethyl)amino-6-nitrobenzene, 1-(2'-hydroxyethyl)amino-2-nitro-4-bis-(2"-hydroxyethyl)aminobenzene, 4-bis-(2'-hydroxyethyl)amino-1-(2"-methoxyethyl)aminonitrobenzene, 1-(2',3'-dihydroxypropyl)amino-2-nitro-4-[methyl-(2"-hydroxyethyl)amino]benzene, 1-[(2',3'-dihydroxypropyl)amino]-2-nitro-4-[ethyl-2"-(hydroxyethyl)amino]benzene, 1-(3'-hydroxypropylamino)-2-nitro-4-bis-(2"-hydroxyethylamino)benzene, 1-amino-4-(2'-hydroxyethyl)aminonitrobenzene, 1-hydroxy-2-amino-4,6-dinitrobenzene, 1-amino-2-nitro-4-bis-(2'-hydroxyethyl) aminobenzene, 1-amino-2-nitro-4-(2'-hydroxyethyl)amino-5-chlorobenzene, 1-(2'-hydroxyethyl)amino-2-nitro-4-aminobenzene, 1-hydroxy-3-nitro-4-aminobenzene,1-(2'-aminoethyl)amino-2-nitro-4-(2"-hydroxyethyl)oxybenzene, 3-nitro-4-(2'-hydroxyethyl)aminophenyl glyceryl ether, 1-amino-5-chloro-4-(2',3'-dihydroxypropyl)-amino-2-nitrobenzene, 1,4-bis-[(2',3'-dihydroxypropyl)amino]-5-chloro-2-nitrobenzene, 1-hydroxy-2-(2'-hydroxyethyl)amino-4,6-dinitrobenzene, 2-amino-6-chloro-4-nitrophenol, 1-hydroxy-3-nitro-4-(3'-hydroxypropylamino)benzene, 3-nitro-4-ethylamino-benzoic acid, 4-amino-2-nitrodiphenylamino-2-carboxylic acid, 2-chloro-6-ethylamino-4-nitrophenol, 2,5-diamino-6-nitropyridine, 1,2,3,4-tetrahydro-6-nitroquinoxaline, 4-(2'-hydroxyethyl)amino-3-nitrobenzonitrile, 4-(2'-hydroxyethyl)amino-3-nitrobenzamide, 1-amino-2-(2'-hydroxyethyl)amino-5-nitrobenzene, 1-methoxy-2-(2'-hydroxyethyl)amino-5-nitrobenzene, 1-hydroxy-3-nitro-4-(2'-hydroxyethyl) aminobenzene, 1-hydroxy-2-amino-3-nitrobenzene, 1-amino-2-methyl-6-nitrobenzene, 1-(2'-hydroxyethyl)oxy-3-methylamino-4-nitrobenzene, 1-methylamino-2-nitro-5-(2',3'-dihydroxypropyl)oxybenzene, 1-(2'-hydroxyethyl)amino-2-hydroxy-4-nitrobenzene, 1-methoxy-3-(2'-aminoethyl)-amino-4-nitrobenzene, 1-(2'-ureidoethyl)amino-4-nitrobenzene, 1-(2'-hydroxyethyl)amino2-nitrobenzene, 4-(2'-hydroxyethyl)amino-3-nitrotrifluoromethylbenzene, 2,4-bis-[N-(2'-hydroxyethyl)amino]-5-chloronitrobenzene, 4-(2',3'-dihydroxypropyl)amino-3-nitrotrifluormethylbenzene, 4-(2'-hydroxymethyl)amino-3-nitromethylbenzene, 4-(2'-Hydroxyethyl)amino-3-nitrochlorobenzene, 1-(4'-nitrophenylazo)-2-methyl-4-bis-(2"-hydroxyethyl)aminobenzene, 1-(3'-nitro-4-amino) phenylazo-2-hydroxy-7-trimethylammonium chloride naphthalene, 1-(2'-hydroxy-4'-sulfo-6'-nitro)-naphthylazo-2-hydroxynaphthalene, 1-(4'-aminophenylazo)-2-methyl-4-bis-[(2'-hydroxyethyl)amino]benzene, 5-(4'-dimethylaminophenylazo)-1,4-dimethyltriazonium chloride, 1-(2'-methoxyphenylazo)-2hydroxy-7-trimethylammonium naphthalene chloride, 1-(4'-aminophenylazo)-2-hydroxy-7-trimethylammonium-naphthalene, 4-(3'-trimethylammoniumphenylazo)-N-phenyl-3-methyl-pyrazolone(5), 4-hydroxy-3-[(4'-sulfo-1'-naphthyl)azo]1-naphthalene sulfonic acid, 1-(4'-sulfophenylazo)-2hydroxynaphthalene, 1-(4'-sulfonphenylazo)-2-hydroxy-6sulfonaphthalene, 4-amino-[4'-bis-(2"-hydroxyethyl)amino]azobenzene, 4-amino-[4'-bis-(2"-hydroxyethyl)amino]-2-methylazobenzene, 3-(2',6'-diaminopyridyl-3'-azo)pyridine, 7-phenylazo-1-amino-3,6-disulfo-8-hydroxynaphthalene, 5-acetylamino-4-hydroxy-3-[(2'-methylphenyl)azo]-2,7-naphthalene disulfonic acid, 2-(2',4'-dimethylphenylazo)-6-(4"-sulfophenylazo)-1,3-dihydroxybenzene, 1,4-bis-(2',3'-dihydroxypropyl) aminoanthraquinone, 1-methylamino-4-(2'-hydroxyethyl)aminoanthraquinone, 2-(2'-aminoethyl)aminoanthraquinone, 2-bromo-4,8-diamino-6-(3'-trimethylammonium)phenylamino-1,5-naphthoquinone, 1-(2'-sulfo-4'-methylphenyl)amino-4-hydroxyanthraquinone, 1,4-diaminoanthraquinone, 1-amino-2-sulfo-4-cyclohexylamino-anthraquinone, 1-methylamino-4-aminopropylaminoanthraquinone, 1-aminopropylaminoanthraquinone, 4',4",4'''-triamino-3-methyl-triphenylcarbonium chloride, bis-(4,4-diethylaminophenyl)-4'-ethylaminonaphthylcarbonium chloride, bis-(4,4-dimethylaminophen)-4'-phenylaminonaphthylcarbonium chloride and 4,4-bis-(N-ethyl-3-sulfobenzyl)amino-2"-sulfofuchsonium.

The aforementioned direct-dyeing dye compounds can be contained in the dye composition according to the invention in a total amount of from about 0.001 to 15 percent by weight, advantageously from 0.3 to 10 percent by weight.

Furthermore the cream-like dye-containing suspension also contains standard cosmetic ingredients used in this type of composition, e.g. perfume oil, animal dye ingredients, such as cochineal (dried female insects Coccus cacti) or Lac dyes, non-dyeing vegetable ingredients, such as dried and pulverized acacia leaves, linden leaves, birch leaves, wheat, rye, barley, licorice, catechu or sage herb; thickeners, such as celluloses, alginates, polysaccharides or mineral thickeners, such as bentonite; surfactants and emulsifiers, antioxidants, such as butyl hydroxyanisole, butyl hydroxytoluene or tocopherol, fruit extracts, chelating agents or solvating agents, such as polyethylene glycols, e.g. polyethylene glycol(4).

As thickeners from the cellulose group, alginates and polysaccharides are used, preferably methyl celluloses, ethyl celluloses, hydroxyethyl celluloses, methylhydroxyethyl celluloses, methylhydroxypropyl celluloses, carboxymethyl celluloses, alginic acid, sodium alginate, ammonium alginate, calcium alginate, gum arabic, guar gum or xanthan gum, as well as the cationic derivatives of the aforementioned compounds, alone or in combination. From 0.1 to 15 percent by weight, advantageously from 0.2 to 10 percent by weight, of these thickeners are contained in the composition according to the invention.

Cationic, anionic, nonionic or amphoteric surfactants and O/W or W/O emulsifying agents, such as silicon surfactants, alkyl ether phosphates, glyceride alkoxylates, alkylsulfates, alkylethersulfates, alkylsulfoacetates, ethoxylated fatty acid esters, fatty alcohol alkoxylates and alkali metal salts or alkaline earth metal salts of fatty acids, can be used as the surfactants and emulsifiers. These surfactants and emulsifiers may be used in an amount of from 0.1 to 20 percent by weight, advantageously from 0.5 to 10 percent by weight, based on the total amount of dye-containing suspension.

To adjust the pH of the dye-containing suspension according to the invention, the suspension can contain alkalizing agents, such as alkali metal hydroxides, sodium carbonates, sodium hydrogen carbonates, magnesium carbonates, ammonium carbonates, ammonium hydrogen carbonates or sodium silicates, or acidifying agents, such as citric acid, tartaric acid, ammonium chloride or ammonium sulfate.

Prior to application the cream-like dye-containing suspension is mixed with cold or warm water (T=10° to 90° C.)

to form an applicable dye-containing slurry or paste. This mixing can occur in a vessel or by shaking in an applicator flask.

The mixture ratio of the dye-containing suspension to water preferably amounts to from 10:1 to 1:10.

The ready-to-use dye composition ("dye slurry") so obtained is applied uniformly to the hair and, after an acting time of 5 to 80 minutes, preferably 15 to 60 minutes, at room temperature (20° to 25° C.) or 10 to 50 minutes with heating (30° to 50° C.). Then the dye-containing suspension is rinsed out of the hair with water and the hair is dried. However it is also possible to apply the dye-containing suspension to the hair moistened previously with water.

The creamy dye-containing suspension can be filled in tubes or cups according to its viscosity, is dust-free and characterized by good miscibility, applicability, distributability and adherence to the hair and outstanding hair dyeing properties.

The following examples illustrate the subject matter in greater detail, but their details should not be considered as limiting the scope of the appended claims.

EXAMPLES

Example 1
creamy Dye-containing Suspension 45.0 g isopropyl palmitate
38.5 g henna leaves, dried and ground
10.0 g sodium carbonate
3.0 g polyethylene glycol(35) castor oil (Cremophor EL of BASF)
1.5 g cationic guar gum (guar hydroxypropyl-trimonium chloride)
1.4 g 3-[(4'-amino-2'-chloro-5'-nitrophenyl)amino]-1,2-propandiol (HC Red No. 10)
0.6 g 3,3'-[(2"-chloro-5"-nitro-1",4"-phenylene)diamino]-bis-1,2-propandiol (HC Red No. 11)
100.00 g 25 g of the above-described dye-containing suspension are stirred with 75 g of warm water (T=40° C.) to form a homogeneous dye paste in a vessel with a brush or an egg beater. The dye paste so obtained is applied uniformly with a brush to bright blond hair. Subsequently the hair is covered with a sheet and heated 40 minutes at 40° C. with a drying hood or heat radiating device. Then the hair is rinsed with warm water and dried.

The dyed hair has an intense red-orange-blond hair color as a result of this dye treatment.

Example 2
Creamy Dye-containing Suspension 43.0 g castor oil
38.5 g henna leaves, dried and ground
10.0 g sodium hydrogen carbonate
5.0 g tetraoxyethylene lauryl ether triphosphate (Hostaphat KL 340 N of Hoechst-Celanese Corp.)
1.5 g sodium alginate
1.0 g 2-(4'-amino-3'-nitroanilino)-ethanol (HC Red No. 12)
0.7 g 3-[(4'-amino-2'-chloro-5'-nitrophenyl)amino]-1,2-propandiol (HC Red No. 10)
0.3 g 3,3'-[(2"-chloro-5"-nitro-1",4"-phenylene)diamino]-bis-1,2-propandiol (HC Red No. 11)
100.00 g 30 g of the above-described dye-containing suspension are stirred with 60 g of hot water (T=70° C.) to form a homogeneous dye paste in a vessel with a brush or an egg beater. The dye paste so obtained is applied uniformly with a brush to dark blond hair (50% gray scale). Subsequently the hair is covered with a sheet and heated 40 minutes at 40° C. with a drying hood or heat radiating device. Then the hair is rinsed with warm water and dried.

The dyed hair has an intense blue-red hair color as a result of this dye treatment, with a color coverage of about 30%.

All percentages, unless otherwise indicated, are percentages by weight.

While the invention has been illustrated and described as embodied in a composition and process for dyeing keratin fibers, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

What is claimed is:

1. A composition for dyeing keratin fibers, said composition comprising from 35 to 75 percent by weight of at least one powdery vegetable dye material; from 25 to 65 percent by weight of at least one oil; and from 0.001 to 15 percent by weight of at least one synthetic direct-dyeing dye compound selected from the group consisting of nitro dye compounds, azo dye compounds, quinone dye compounds and triphenylmethane dye compounds.

2. The composition as defined in claim 1, wherein said at least one powdery vegetable dye material is selected from the group consisting of henna leaves, indigo leaves, camomile, curcuma roots, rhubarb, black alder tree bark, olive leaves, Canadian bloodroot, curcuma, fustic, redwood, red sandalwood, haematoxylon wood, madder root, black elder berries and black apple berries.

3. The composition as defined in claim 1, wherein said at least one oil is selected from the group consisting of liquid silicones, liquid paraffins, vegetable oils, animal oils, liquid fatty acids, liquid fatty acid esters, liquid alkoxylated fatty acid esters, liquid glycerides, liquid alkoxylated glycerides, liquid fatty alcohols, liquid alkoxylated fatty alcohols, liquid nonylphenol ether, liquid polyethylene glycols and liquid polypropylene glycols.

4. The composition as defined in claim 1, wherein said at least one oil is selected from the group consisting of paraffinum perliquidum, paraffinum subliquidum, dimethicone, cyclomethicone, isopropyl palmitate, hexyl laurate, dibutyl adipate, octyl palmitate, polyethylene glycol (7) glycerylcocoate, isopropyl myristate, isopropyl stearate, trioxyethylene lauryl ether, dioxyethylene lauryl ether, sunflower oil, spermaceti oil, olive oil and castor oil.

5. The composition as defined in claim 1, further comprising a member selected from the group consisting of anionic surfactants, cationic surfactants, nonionic surfactants and amphoteric surfactants.

6. The composition as defined in claim 1, further comprising a member selected from the group consisting of anionic emulsifiers, cationic emulsifiers, nonionic emulsifiers and amphoteric emulsifiers.

7. A method for dyeing of hair, said method comprising the steps of:

a) mixing a dye-containing suspension containing 35 to 75 percent by weight of at least one powdery vegetable dye ingredient; 25 to 65 percent by weight of at least one sythetic oil and from 0.001 to 15 percent by weight of at least one synthetic direct-dyeing dye compound selected from the group consisting of nitro dye compounds, azo dye compounds, quinone dye compounds and triphenylmethane dye compounds, with water in a ratio of 10:1 to 1:10 to form a dye paste;

b) subsequently applying said dye paste uniformly to the hair;

c) allowing said dye paste applied to the hair to act on the hair for an acting-time of 5 to 80 minutes; and d) then rinsing the hair with water and subsequently drying the hair.

8. The method as defined in claim 7, wherein said dye paste acts on the hair at room temperature and said acting time is from 15 to 60 minutes.

9. The method as defined in claim 7, further comprising heating the hair when said dye paste acts on the hair and wherein said acting time is from 10 to 50 minutes.

10. The method as defined in claim 7, wherein said at least one powdery vegetable dye ingredient is selected from the group consisting of henna leaves, indigo leaves, camomile, curcuma roots, rhubarb, black alder tree bark, olive leaves, Canadian bloodroot, curcuma, fustic, redwood, red sandalwood, haematoxylon wood, madder root, black elder berries and black apple berries.

11. The method as defined in claim 7, wherein said at least one oil is selected from the group consisting of liquid silicones, liquid paraffins, vegetable oils, animal oils, liquid fatty acids, liquid fatty acid esters, liquid alkoxylated fatty alcohols, liquid nonylphenol ethers, liquid polyethylene glycols and liquid polypropylene glycols.

* * * * *